US009636005B2

United States Patent
Yoshino

(10) Patent No.: US 9,636,005 B2
(45) Date of Patent: May 2, 2017

(54) ENDOSCOPE SYSTEM HAVING LIGHT INTENSITY ADJUSTMENT WITH MOVABLE OPTICAL SYSTEM

(71) Applicant: OLYMPUS CORPORATION, Tokyo (JP)

(72) Inventor: Masahiro Yoshino, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/132,319

(22) Filed: Apr. 19, 2016

(65) Prior Publication Data

US 2016/0227992 A1   Aug. 11, 2016

Related U.S. Application Data

(63) Continuation of application No. PCT/JP2015/055120, filed on Feb. 24, 2015.

(30) Foreign Application Priority Data

Jun. 9, 2014   (JP) ................................. 2014-118803

(51) Int. Cl.
*A61B 1/00* (2006.01)
*A61B 1/04* (2006.01)
(Continued)

(52) U.S. Cl.
CPC ........ *A61B 1/0638* (2013.01); *A61B 1/00006* (2013.01); *A61B 1/00009* (2013.01);
(Continued)

(58) Field of Classification Search
CPC ........... A61B 1/06; A61B 1/0638; A61B 1/00; A61B 1/04; A61B 1/07; A61B 1/00117;
(Continued)

(56) References Cited

U.S. PATENT DOCUMENTS 5,749,830 A   5/1998   Kaneko et al.
6,432,047 B1 *  8/2002   Gust ...................... A61B 1/042
                                                      385/117
(Continued)

FOREIGN PATENT DOCUMENTS

EP      2353490 A1     8/2011
JP    H07-222712 A     8/1995
(Continued)

OTHER PUBLICATIONS

International Search Report dated May 19, 2015 issued in PCT/JP2015/055120.

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

An endoscope system includes an optical transmission section that is provided in an endoscope inserted into an interior of a subject and transmits illuminating light to a distal end, a light source section that generates light, a first lens section that receives the light, from the light source section and emits the light with characteristics of different spatial intensity distributions, a second lens section that causes the light emitted from the first lens section to enter the proximal end of the optical transmission section, a distance adjusting section that can adjust a distance, and a control section that controls the distance adjusting section that adjusts the distance between the first lens section and the second lens section so that amounts of the light of a first and second wavelength bands have a predetermined ratio of amount of light.

11 Claims, 8 Drawing Sheets

(51) Int. Cl.
*A61B 1/06* (2006.01)
*A61B 1/07* (2006.01)

(52) U.S. Cl.
CPC ............ *A61B 1/00096* (2013.01); *A61B 1/06* (2013.01); *A61B 1/063* (2013.01); *A61B 1/0684* (2013.01); *A61B 1/07* (2013.01)

(58) Field of Classification Search
CPC ............ A61B 1/00121; A61B 1/00126; A61B 1/00163; A61B 1/00165; A61B 1/00167; A61B 1/00188; A61B 1/0019; G02B 6/38; G02B 6/40
USPC ....... 600/109, 132, 136, 160, 167, 168, 172, 600/175, 176, 178, 182; 385/54, 55, 100, 385/116, 117; 348/65
See application file for complete search history.

(56) References Cited

U.S. PATENT DOCUMENTS

| | | | | |
|---|---|---|---|---|
| 2011/0071349 | A1* | 3/2011 | Drontle | A61B 1/00165 600/106 |
| 2011/0184244 | A1 | 7/2011 | Kagaya et al. | |
| 2014/0111628 | A1* | 4/2014 | Yoshino | H04N 5/23296 348/65 |
| 2015/0168710 | A1* | 6/2015 | Zobel | A61B 1/00105 348/45 |

FOREIGN PATENT DOCUMENTS

| | | |
|---|---|---|
| JP | H08-054515 A | 2/1996 |
| JP | H09-182714 A | 7/1997 |
| JP | 2003-135380 A | 5/2003 |
| JP | 2011/152371 A | 8/2011 |
| WO | WO 00/49938 A1 | 8/2000 |

\* cited by examiner

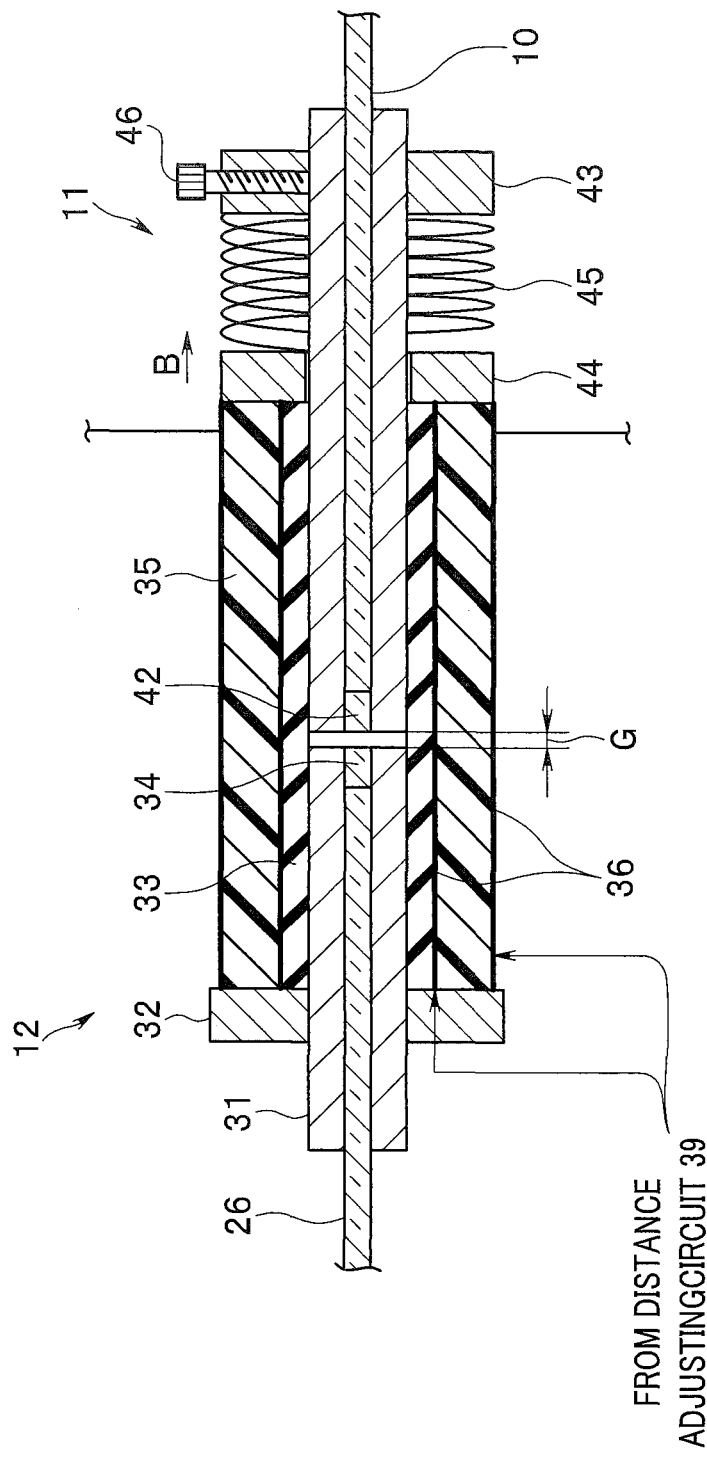

| GAP | b | | | d | | |
|---|---|---|---|---|---|---|
| LASER MAX OUTPUT VALUE (mW) | 10 | 10 | 10 | 10 | 10 | 10 |
| LASER MIN OUTPUT VALUE (mW) | 1.0 | 1.0 | 1.0 | 1.0 | 1.0 | 1.0 |
| WAVELENGTH | BLUE | GREEN | RED | BLUE | GREEN | RED |
| CONNECTION EFFICIENCY | 0.14 | 0.24 | 0.50 | 0.05 | 0.09 | 0.20 |
| LASER OUTPUT VALUE (mW) | 3.6 | 2.1 | 1.0 | 4.0 | 2.2 | 1.0 |
| AMOUNT OF ILLUMINATING LIGHT (mW) | 0.5 | 0.5 | 0.5 | 0.2 | 0.2 | 0.2 |

FIG. 6

| GAP | c | | | d | | |
|---|---|---|---|---|---|---|
| LASER MAX OUTPUT VALUE (mW) | 20 | 15 | 10 | 20 | 15 | 10 |
| LASER MIN OUTPUT VALUE (mW) | 2.0 | 1.5 | 1.0 | 2.0 | 1.5 | 1.0 |
| WAVELENGTH | BLUE | GREEN | RED | BLUE | GREEN | RED |
| CONNECTION EFFICIENCY | 0.1 | 0.2 | 0.4 | 0.05 | 0.09 | 0.20 |
| LASER OUTPUT VALUE (mW) | 4.0 | 2.0 | 1.0 | 4.0 | 2.2 | 1.0 |
| AMOUNT OF ILLUMINATING LIGHT (mW) | 0.4 | 0.4 | 0.4 | 0.2 | 0.2 | 0.2 |

FIG. 7

| GAP | d | | | c | | |
|---|---|---|---|---|---|---|
| LASER MAX OUTPUT VALUE (mW) | 10 | 15 | 20 | 10 | 15 | 20 |
| LASER MIN OUTPUT VALUE (mW) | 1.0 | 1.5 | 2.0 | 1.0 | 1.5 | 2.0 |
| WAVELENGTH | BLUE | GREEN | RED | BLUE | GREEN | RED |
| CONNECTION EFFICIENCY | 0.05 | 0.09 | 0.2 | 0.1 | 0.2 | 0.4 |
| LASER OUTPUT VALUE (mW) | 4.0 | 3.3 | 2.0 | 4.0 | 3.0 | 2.0 |
| AMOUNT OF ILLUMINATING LIGHT (mW) | 0.2 | 0.3 | 0.4 | 0.4 | 0.6 | 0.8 |

ENDOSCOPE SYSTEM HAVING LIGHT INTENSITY ADJUSTMENT WITH MOVABLE OPTICAL SYSTEM

CROSS REFERENCE TO RELATED APPLICATION

This application is a continuation application of PCT/JP2015/055120 filed on Feb. 24, 2015 and claims benefit of Japanese Application No. 2014-118803 filed in Japan on Jun. 9, 2014, the entire contents of which are incorporated herein by this reference.

BACKGROUND OF THE INVENTION

1. Field of the Invention

The present invention relates to an endoscope system provided with a function of adjusting an amount of illuminating light.

2. Description of the Related Art

In recent years, endoscopes have been widely used in a medical field or the like. Furthermore, when observing an interior of a subject, endoscope systems provided with a function of adjusting an amount of illuminating light are adopted so as to obtain images with brightness which are easy to observe.

For example, a prior art in Japanese Patent Application Laid-Open Publication No. 2003-135380 discloses that in a case where light from a light source is condensed by a condensing optical system and caused to enter an incident end face of a light guide, at least one of the light source and the condensing optical system is enabled to move along an optical axis of the condensing optical system.

The above-described prior art discloses contents when illuminating light of the light source is caused to efficiently enter the incident end face of the light guide.

SUMMARY OF THE INVENTION

An endoscope system according to an aspect of the present invention includes an optical transmission section that is provided in an endoscope inserted into an interior of a subject, transmits illuminating light incident on a proximal end to a distal end and emits the illuminating light from the distal end to illuminate the interior of the subject, a light source section that generates light of a first wavelength band and light of a second wavelength band which is different from the light of the first wavelength band as the illuminating light for illuminating the interior of the subject, a first lens section that receives, as incident light, the light of the first wavelength band and the light of the second wavelength band generated by the light source section and emits the light with characteristics of different spatial intensity distributions in accordance with wavelengths, a second lens section that is provided opposite to the first lens section, receives, as incident light, at least part of the light emitted from the first lens section and causes the received light to enter the proximal end of the optical transmission section, a distance adjusting section that can adjust a distance between the first lens section and the second lens section, and a control section that controls the distance adjusting section that adjusts the distance between the first lens section and the second lens section so that an amount of the light of the first wavelength band and an amount of the light of the second wavelength band emitted into the interior of the subject have a predetermined ratio of amount of light.

BRIEF DESCRIPTION OF THE DRAWINGS

FIG. 2B is a diagram illustrating the illuminating light connector and the illuminating light connector receptacle structure which are connected together;

FIG. 6 is a diagram illustrating, in a table form, specific examples of cases where the amount of illuminating light is adjusted using laser light sources having different minimum output values; and FIG. 7 is a diagram illustrating, in a table form, specific examples of cases where light beams of the respective wavelengths of the laser light sources are set to different amounts of illuminating light.

DETAILED DESCRIPTION OF THE PREFERRED EMBODIMENTS

Hereinafter, embodiments of the present invention will be described with reference to the accompanying drawings.

First Embodiment

Figure 1:
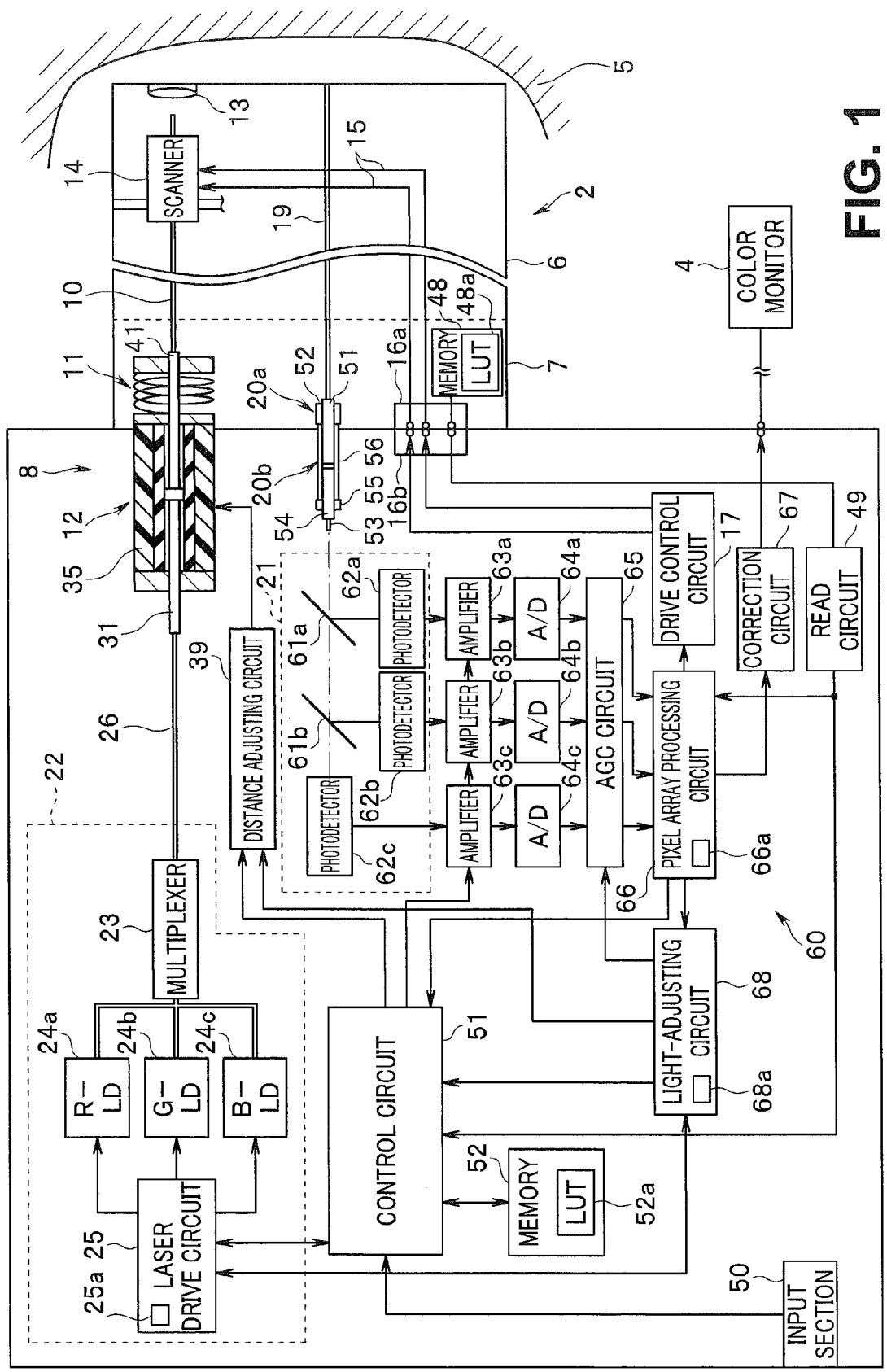
FIG. 1 is a diagram illustrating an overall configuration of an endoscope system according to a first embodiment of the present invention.

As shown in FIG. 1, an endoscope system 1 according to a first embodiment of the present invention includes a scanning type endoscope 2, an endoscope apparatus body (hereinafter simply referred to as "body") 3 to which the scanning type endoscope 2 is detachably connected and a color monitor 4 as a display apparatus that displays an image generated by the body 3 as an endoscope image.

The scanning type endoscope 2 includes an elongated insertion portion 6 inserted into an interior of a subject 5 and a connector 7 provided at a rear end (proximal end) of the insertion portion 6, and the connector 7 is detachably connected to a connector receptacle 8 of the body 3. Note that the connector 7 includes an illuminating light connector 11, an electric connector 16a and a light-receiving connector 20a as will be described below, and the connector receptacle 8 includes an illuminating light connector receptacle 12, an electric connector receptacle 16b and a light-receiving connector receptacle 20b.

An illumination optical fiber 10 making up an optical transmission section that transmits illuminating light along a longitudinal direction of the insertion portion 6 is inserted into the insertion portion 6. The illumination optical fiber 10 is made of a single-mode fiber. A proximal end of the illumination optical fiber 10 is fixed to the illuminating light connector (or plug) 11 and the illuminating light connector 11 is detachably connected to the illuminating light connector receptacle 12 of the body 3.

The illumination optical fiber 10 transmits illuminating light incident from the illuminating light connector receptacle 12 side of the body 3 on the proximal end of the illumination optical fiber 10 to a distal end and emits the illuminating light through an illumination lens 13 disposed opposite to the distal end into the interior of the subject 5 ahead of the illumination lens 13.

A periphery of the distal end of the illumination optical fiber 10 is held by a scanner (or scanning actuator) 14 and when an axial direction of the illumination optical fiber is assumed to be, for example, a Z direction, two drive signals are applied to the scanner 14 to drive the scanner 14 in two X and Y directions which are orthogonal to the Z direction, and the scanner 14 thereby vibrates the held distal end of the illumination optical fiber 10 in two orthogonal directions within an XY plane. By vibrating the distal end of the illumination optical fiber 10 in two orthogonal directions, the illuminating light emitted from the distal end of the illumination optical fiber 10 via the illumination lens 13 is radiated onto the subject 5 as an optical spot, which is scanned two-dimensionally along, for example, a spiral track. Note that the scanner 14 is constructed of two piezoelectric elements which are driven in two directions or four piezoelectric elements made up of two pairs of two piezoelectric elements. A proximal end of the scanner 14 is fixed to an inner wall surface of the insertion portion 6 by a support member.

A distal end of a signal line 15 inserted into the insertion portion 6 is connected to the scanner 14 and the electric connector 16a provided at a proximal end of the signal line 15 is connected to a drive control circuit 17 that generates a drive signal via the electric connector receptacle 16b of the body 3 to which the electric connector 16a is connected.

Furthermore, in the insertion portion 6, a light-receiving optical fiber 19 that detects (receives) reflected light of illuminating light reflected on the subject 5 side and transmits the detected (received) light is inserted along the longitudinal direction of the insertion portion 6. A distal end of the light-receiving optical fiber 19 is exposed to a distal end surface of the insertion portion 6, forming an incident window (detection window) that receives reflected light. Light incident on the distal end of the light-receiving optical fiber 19 is transmitted to a proximal end thereof and the light-receiving connector 20a is provided at the proximal end.

The light-receiving connector 20a is connected to the light-receiving connector receptacle 20b provided in the body 3 and the light transmitted from the light-receiving connector 20a to the light-receiving connector receptacle 20b is converted to an electric signal by a photodetection section (or photodetection unit) 21 in the body 3.

The body 3 includes a light source section (or light source unit) 22 that generates light beams of three different wavelength bands and includes a multiplexer 23 that combines (multiplexes) the generated light beams of three wavelength bands.

The light source section 22 includes a red color laser diode (abbreviated as "R-LD" in FIG. 1) 24a, a green color laser diode (abbreviated as "G-LD" in FIG. 1) 24b, and a blue color laser diode (abbreviated as "B-LD" in FIG. 1) 24c, which generate three red, green and blue laser light beams as light beams of three wavelength bands. In the light source section 22, for example, the laser diode 24a generates light of a red wavelength band as a first light source that generates light of a first wavelength band, the laser diode 24b or 24c generates light of a green or blue wavelength band as a second light source that generates light of a second wavelength band. Note that the laser diodes 24b and 24c may also be called "second and third light sources" that generate second and third light respectively.

The laser diodes 24a, 24b and 24c generate light beams of three red, green and blue wavelength bands respectively as illuminating light when laser drive signals are applied thereto from the laser drive circuit 25, transmit the respective light beams to the multiplexer 23 via the respective optical fibers and the multiplexer 23 multiplexes the three light beams and transmits them to the distal end side through one optical fiber 26. The illuminating light connector receptacle 12 is provided on the distal end side of the optical fiber 26.

The laser drive circuit 25 includes a light amount adjusting circuit 25a that forms a light amount adjusting section for adjusting amounts of laser light emitted by the laser diodes 24a, 24b and 24c. The light amount adjusting circuit 25a adjusts the amplitude (peak value) of a laser drive signal which is outputted in a pulse form, and thereby respectively adjusts the amounts of light emitted from the laser diodes 24a, 24b and 24c to which laser drive signals are applied. According to the present embodiment, laser drive signals are simultaneously applied to the three laser diodes 24a, 24b and 24c, and the three laser diodes 24a, 24b and 24c emit light simultaneously.

Figure 2A:
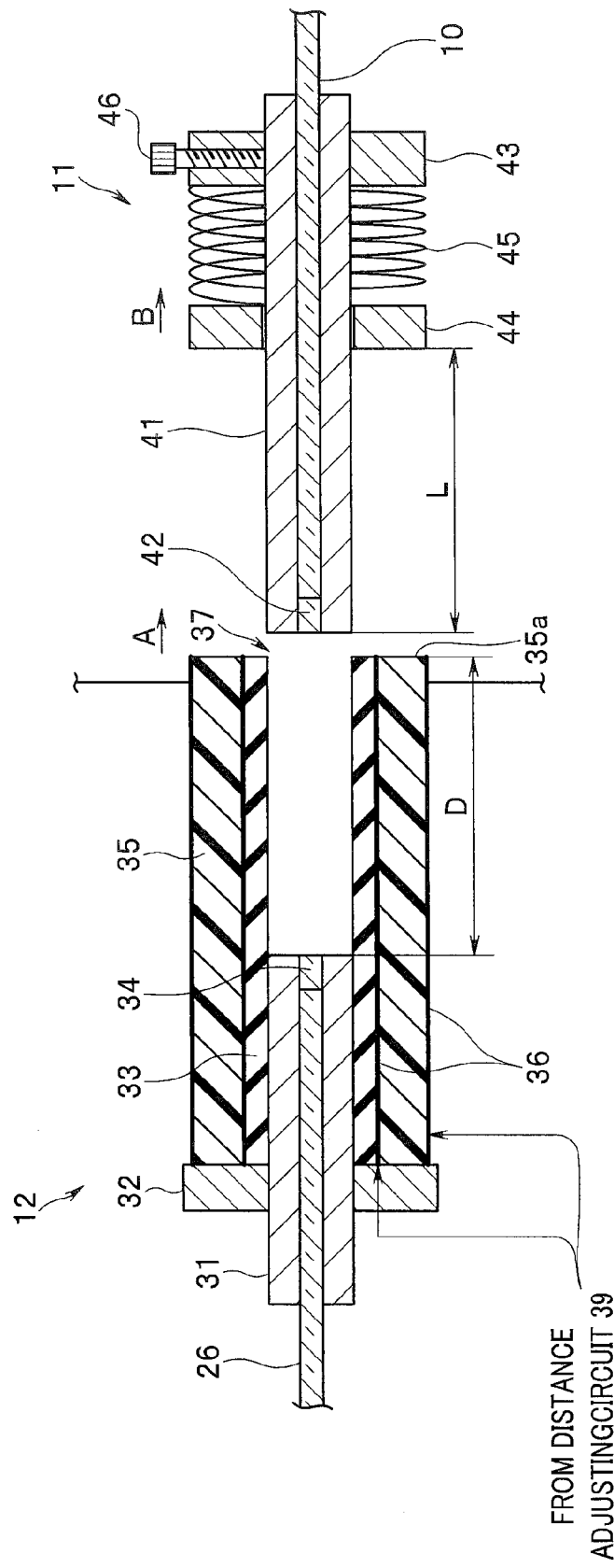
FIG. 2A is a diagram illustrating an illuminating light connector and an illuminating light connector receptacle structure which are not connected together.

The illuminating light connector receptacle 12 of the body 3 and the illuminating light connector 11 of the scanning type endoscope 2 have a structure as shown in FIG. 2A and FIG. 2B. Note that FIG. 2B illustrates the illuminating light connector 11 in FIG. 2A attached (connected) to the illuminating light connector receptacle 12.

With the distal end side of the optical fiber 26 being protected by a ferrule 31 as a cylindrical protective member that protects the optical fiber 26, the optical fiber 26 penetrates a hole provided in a flange 32 in the vicinity of the proximal end of the connector receptacle 12 and extends in a cylindrical body (sleeve) 33 having a C-shaped-ring cross section and formed of an elastic member having enough elasticity. A first lens 34 that has a function as a convex lens for condensing light or a concave lens that expands light (forming a first lens section) is provided on a distal end face that forms a light emission end face of the optical fiber 26.

A distal end side of the optical fiber 26 protected by the ferrule 31 is disposed along the central hole of the cylindrical body 33, a distal end face on which the first lens 34 is provided together with a distal end face of the ferrule 31 is positioned in the vicinity of the center position of the cylindrical body 33 in the longitudinal direction and the ferrule 31 is fixed in the hole of the flange 32.

A piezoelectric element 35 having a cylindrical shape and an appropriate thickness is disposed outside the cylindrical body 33 and electrodes 36, 36 are provided on cylindrical inner and outer circumferential surfaces of the piezoelectric element 35 respectively. A voltage is applied between the electrodes 36, 36 of the piezoelectric element 35 facing each other in a thickness direction and an electric field is applied in the thickness direction thereof to thereby make the length of the piezoelectric element 35 in the longitudinal direction variable. In the present embodiment, proximal ends of the cylindrical body 33 and the cylindrical piezoelectric element 35 are fixed to the flange 32 so that a position of a distal end face 35a of the piezoelectric element 35 in the longitudinal direction may be made variable according to a voltage (value) applied to the piezoelectric element 35.

For example, the state shown in FIG. 2A is one in which no voltage is applied to the piezoelectric element 35, and if a voltage is applied in this state, the distal end face 35a of the piezoelectric element 35 expands in a direction shown by an arrow A. A voltage for distance adjustment generated by a distance adjusting circuit 39 in the body 3 is applied to the piezoelectric element 35.

An insertion holding section 37 that positions and holds the illuminating light connector 11 is formed in a columnar opening of the cylindrical body 33 opposite to the distal end face of the optical fiber 26 on which the ferrule 31 and the first lens 34 are provided.

The illuminating light connector 11 inserted into the insertion holding section 37 includes a ferrule 41 as a cylindrical protective member that protects a periphery of an incident end on the proximal end side of the illumination optical fiber 10. Furthermore, a second lens 42 that includes a function as a convex lens that condenses light or as a concave lens that expands light (forming a second lens section) is provided on a distal end face that forms an incident end face of light in the illumination optical fiber 10.

A first flange 43 which the ferrule 41 penetrates and is fixed to is provided at a position close to an end which is a forward side of the incident end face in the longitudinal direction of the ferrule 41. A second flange 44 provided with a hole through which the ferrule 41 is movable in the longitudinal direction is disposed on the proximal end side opposite to the first flange 43, and the first flange 43 and the second flange 44 are connected together via a coil-shaped spring 45 which has elasticity in the longitudinal direction.

The spring 45 has a coil shape with an outside diameter larger than an outside diameter of at least the ferrule 41 outside the outer circumferential face of the ferrule 41, one end of which is fixed to the first flange 43 and the other end of which is fixed to the second flange 44. That is, the second flange 44 is elastically held to the first flange 43 fixed to the ferrule 41 by the spring 45 as an elastic member. Therefore, when a force for pressing the second flange 44 toward the first flange 43 side is applied to the second flange 44, the second flange 44 moves in a direction shown by an arrow B.

Furthermore, a portion of the ferrule 41 shown by a length L from the proximal end face of the second lens 42 to the proximal end face of the second flange 44 in the illuminating light connector 11 is a portion inserted into the insertion holding section 37 of the illuminating light connector receptacle 12 and the length L is set in correspondence with a distance D from the distal end face (emission end face) of the first lens 34 to the distal end face 35a of the piezoelectric element 35 (also referred to as "length of the insertion holding section 37") (more specifically, the length L is set to a value slightly smaller than the distance D).

Furthermore, a screw 46 as a fixed position adjusting member is provided in the first flange 43, and the screw 46 makes adjustable the fixed position of the first flange 43 in the longitudinal direction of the ferrule 41 so that the length L may be adjusted.

The state shown in FIG. 2A is changed to a state shown in FIG. 2B when the ferrule 41 of the illuminating light connector 11 is inserted into the insertion holding section 37 of the illuminating light connector receptacle 12 to set an attached state in which the second flange 44 comes into contact with the distal end face 35a of the piezoelectric element 35.

As shown in FIG. 2B, the first lens 34 and the second lens 42 face each other with a small distance (gap) G, and illuminating light emitted from the distal end face (emission end face) of the optical fiber 26 via the first lens 34 is condensed by the second lens 42 and is incident on the incident end face (proximal end face) of the illumination optical fiber 10 that forms an optical transmission section.

Depending on the size of the gap G between the first lens 34 and the second lens 42, a ratio of light on the optical fiber 26 side transmitted to the illumination optical fiber 10 varies a great deal and the amount of illuminating light emitted from the distal end face of the illumination optical fiber 10 as illuminating light also varies a great deal. In other words, connection efficiency E as a ratio of the amount of light emitted from the distal end face of the illumination optical fiber 10 to the amount of light emitted from the first lens 34 varies a great deal depending on the size of the gap G. For example, when the amount of light emitted from the first lens 34 is assumed to be 1, the amount of light emitted from the distal end face of the illumination optical fiber 10 can be changed over a wide range of amounts of light from a maximum of 1 to 0.1 or less.

When emitting incident light to the second lens 42 side, the first lens 34 preferably exhibits no wavelength dependency, but it generally does have wavelength dependency. When causing the incident light to enter the proximal end of the illumination optical fiber 10, the second lens 42 preferably exhibits no wavelength dependency either, but it generally does have wavelength dependency. That is, the first lens 34 emits light to the second lens 42 side with characteristics of spatial intensity distribution in which a beam waist size, beam waist position or the like spatially differs in accordance with wavelengths. When transmitting illuminating light, the illumination optical fiber 10 that forms an optical transmission section also has wavelength-dependent transmission characteristics.

Figures 3, 4:
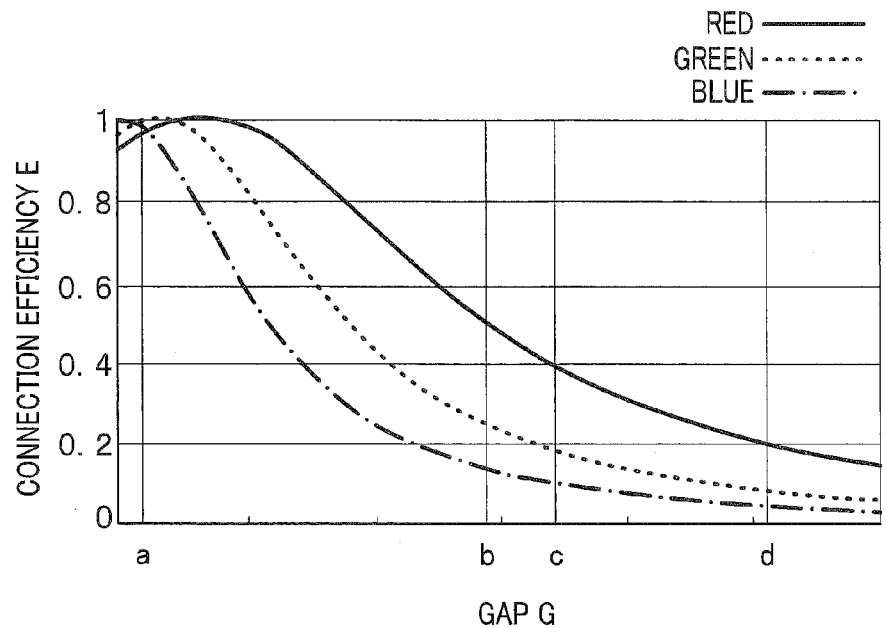
FIG. 3 is a diagram illustrating a relationship between a value of an interval (gap) between an optical plug and an optical receptacle, and connection efficiency that changes in accordance with the gap.
FIG. 4 is a diagram illustrating, in a table form, a specific example of a case where an amount of illuminating light is adjusted with the gap in FIG. 3 set to a specific value.

Therefore, the above-described connection efficiency E demonstrates characteristics that differ depending on the wavelength band of transmitted light. FIG. 3 illustrates a characteristic diagram when the connection efficiency E is measured while changing the value of the gap G in the present embodiment. As shown in FIG. 3, the connection efficiency E has a wavelength dependency and the connection efficiency E has a maximum connection efficiency value of 1 when the gap G is nearly 0 and the value of the connection efficiency E decreases substantially monotonously as the value of the gap G increases. Furthermore, the connection efficiency E demonstrates a characteristic in which it is largest in the red wavelength band (over the entire range of the gap G where the connection efficiency E is smaller than 1), next largest in green and smallest in the blue wavelength band.

In the present embodiment, the value of the gap G in the state shown in FIG. 2B is adjusted in advance so that the connection efficiency E shown by "a" in FIG. 3 becomes substantially 1 by adjusting the fixed position using the screw 46. The distance adjusting circuit 39 applies a distance adjusting voltage to the piezoelectric element 35, the piezoelectric element 35 thereby, for example, expands in accordance with the value of the distance adjusting voltage, presses the flange 44 forward by the length the distal end face 35a of the piezoelectric element 35 expands and causes the illuminating light connector 11 to move in a direction shown by the arrow B. By moving the illuminating light connector 11 and thereby increasing the gap G shown in FIG. 2B, the connection efficiency E can be set to any given value smaller than 1.

Relationship information indicating a relationship between the connection efficiency E and the gap G between both lenses 34 and 42 shown in FIG. 3 is stored in a lookup table (LUT) 48a formed in some storage area in a memory 48 provided inside the connector 7, for example. When the scanning type endoscope 2 is attached (connected) to the body 3, a read circuit 49 reads the relationship information of the LUT 48a and stores the relationship information in a LUT 52a formed in some storage area in a memory 52 via a control circuit 51 in the body 3, for example.

Note that without being limited to the case where the relationship information indicating the relationship with the gap G between both lenses 34 and 42 is stored in the LUT 48a on the connector 7 side, the relationship information may also be stored in the LUT 52a of the body 3 in advance. For example, the scanning type endoscope 2 may be connected to the body 3, the relationship information indicating the relationship with the gap G between both lenses 34 and 42 may be stored in the LUT 52a so as to use the stored relationship information thereinafter.

The memory 48 may also store information on a drive characteristic of the scanner 14. More specifically, the memory 48 may store information on a drive characteristic indicating a characteristic of an amount of vibration (or amount of scanning) of vibrating (scanning) the distal end of the illumination optical fiber 10 with respect to the amplitude of a drive signal applied to the scanner 14, and the drive control circuit 17 may drive the scanner 14 with reference to the information on the drive characteristic.

Moreover, the memory 52 (or LUT 52a) stores information on a characteristic when the piezoelectric element 35 is caused to expand. The information includes the value of a distance adjusting voltage, length by which the piezoelectric element 35 expands or a relationship of moving distance of the distal end face 35a. For this reason, if the value of the gap G to be set is obtained, the value of the distance adjusting voltage to be set for the gap G can be calculated with reference to the information on the characteristic. Furthermore, it is possible to calculate the value of the gap G from the value of the distance adjusting voltage applied to the piezoelectric element 35 or also calculate the connection efficiency. Information on a LUT that associates the value of the gap G with the value of the distance adjusting voltage (with the connection efficiency E) may also be stored in the memory 52 or LUT 52a.

Even when the amounts of light or the output values of amounts (simply "output values") of light emitted from the laser diodes 24a, 24b and 24c of the light source section 22 are set to a minimum (smallest), if the amount of illuminating light is too large, it is enabled to reference the relationship information in the LUT 52a, make the size of the gap G variable and provide light adjustment to obtain an amount of illuminating light suitable for observation using light-adjusting means provided in the body 3.

Ranges from a minimum output value as a minimum amount of light emitted to a maximum output value as a maximum amount of light emitted when the laser diodes 24a, 24b and 24c of the light source section 22 are caused to emit light are 1 to 10 (mW), 1 to 10 (mW), and 1 to 10 (mW) as shown in, for example, FIG. 4 (the minimum output values and the maximum output values in the laser diodes 24a, 24b and 24c are not limited to the values shown in FIG. 4 as will be described later). Therefore, none of the laser diode 24a, 24b or 24c is enabled to emit light at, for example, less than 1 mW which is a minimum output value. For this reason, when the amount of illuminating light is too large even when a minimum output value is set, the amount of illuminating light can be adjusted to a target value by increasing the size of the gap G between both lenses 34 and 42 and decreasing the value of the connection efficiency E.

Since the connection efficiency E has a wavelength dependency, in the present embodiment, the value of the gap G is controlled for light in one wavelength band such as light of the red wavelength band so that the amount of light emitted from the distal end face of the illumination optical fiber 10 which forms an optical transmission section becomes a value of a predetermined amount of light, and the amounts of light emitted from the laser diodes 24b and 24c as light sources are controlled (with reference to the relationship information of the LUT 52a) so that the light of the remaining wavelength bands, more specifically, light of the green and blue wavelength bands satisfies a predetermined ratio of amounts of light. The predetermined ratio of amounts of light in this case may be defined as a ratio of amounts of light of the green and blue wavelength bands to the amount of light of the red wavelength band or as a ratio of amounts of light of three red, green and blue light beams.

FIG. 4 illustrates setting examples of gap values and laser output values when a target amount of illuminating light emitted from the distal end face of the illumination optical fiber 10 is set to 0.5 (mW) and 0.2 (mW) for light of all red, green and blue wavelength bands (so as to have an equal light amount value or an equal ratio of amounts of light) respectively. As will be described below, the value of the gap G is set with reference to light of the red wavelength band in which the connection efficiency E is highest.

For example, while the red laser diode 24a is being set to its minimum output value (1.0 mW), the distance adjusting circuit 39 adjusts the value of the gap G so that the amount of red illuminating light becomes a target amount of illuminating light. When the target amount of illuminating light is 0.5 (mW), the value of the gap G is set to a value b (see FIG. 3) at which the connection efficiency E becomes 0.5 when the red laser diode 24a is likewise set to a minimum output value (1.0 mW).

When the gap G is the value b, it is calculated from the LUT 48a that the connection efficiency E of the green laser diode 24b becomes 0.24, and (the light amount adjusting circuit 25a of) the laser drive circuit 25 adjusts the amount of light emitted so that the target amount of illuminating light becomes 0.5 (mW) and the output value becomes 2.1 (mW).

On the other hand, when the gap G is the value b, it is calculated from the LUT 48a that the connection efficiency E of the blue laser diode 24c becomes 0.14, and (the light amount adjusting circuit 25a of) the laser drive circuit 25 adjusts the amount of light emitted so that the target amount of illuminating light becomes 0.5 (mW) and the output value becomes 3.6 (mW).

When the target amount of illuminating light is 0.2 (mW), while the red laser diode 24a is being set to a minimum output value (1.0 mW), the gap G thereof is set to a value d (see FIG. 3) at which the connection efficiency E becomes 0.2 for light of the red laser diode 24a.

When the gap G is a value d, it is calculated from the LUT 48a that the connection efficiency E of the green laser diode 24b becomes 0.09, and (the light amount adjusting circuit 25a of) the laser drive circuit 25 adjusts the amount of light emitted so that the target amount of illuminating light becomes 0.2 (mW) and the output value becomes 2.2 (mW).

On the other hand, when the gap G is the value d, it is calculated from the LUT 48a that the connection efficiency E of the blue laser diode 24c becomes 0.05, and (the light amount adjusting circuit 25a of) the laser drive circuit 25 adjusts the amount of light emitted so that the target amount of illuminating light becomes 0.2 (mW) and the output value becomes 4.0 (mW).

According to the present embodiment, as described above, it is possible to adjust (set) amounts of illuminating light of a plurality of wavelength bands emitted from the distal end face of the illumination optical fiber 10 so as to have predetermined amounts of light respectively and also adjust the amounts of illuminating light of the plurality of wavelength bands so as to have a predetermined ratio of amounts of light. Furthermore, according to the present embodiment, as will be described later, it is also possible to adjust (set) the amounts of illuminating light of a plurality of wavelength bands emitted from the distal end face of the illumination optical fiber 10 to an amount of light (a predetermined ratio of amount of light) that satisfies a condition corresponding to target brightness of an image based on brightness of an image signal (image) generated by the image processing section (or image processing section) 60 of the body 3.

When the value of the gap G is changed so as to be larger by a predetermined amount, for example, on the order of 10 to several tens of µm, the light-adjusting circuit 68 or the control circuit 51 has a function as a light amount ratio adjusting section or a light amount ratio adjusting circuit that adjusts the amounts of light of a plurality of wavelength bands emitted from the distal end face of the illumination optical fiber 10 so as to keep a predetermined ratio of amount of light.

When the value of the gap G is changed so as to be larger by a predetermined amount, for example, on the order of 10 to several tens of µm, and changed so that the amount of red light emitted from the distal end face of the illumination optical fiber 10 is decreased, for example, the light-adjusting circuit 68 controls operation of the light amount adjusting circuit 25*a* and the light amount adjusting circuit 25*a* adjusts the amounts of light emitted of the green and blue laser diodes 24*b* and 24*c* so as to keep the ratio of amounts of red, green and blue light before the gap G is changed.

The memory 48 may be configured to store drive-related information such as light-emission timing associated with a drive waveform or a track of a predetermined spiral shape (of a drive signal) so that the scanner 14 vibrates the distal end of the illumination optical fiber 10 and forms an optical spot along the track of the predetermined spiral shape. In this case, the drive-related information is stored, for example, in the memory 52 via the read circuit 49 in the body 3 and the control circuit 51 controls laser drive operation of the laser drive circuit 25 with reference to the drive-related information.

Note that the present invention is not limited to the example in which the drive-related information is stored in the memory 48, but the drive-related information may be stored in the memory 52 on the body 3 side in advance.

The light-receiving connector 20*a* provided at a proximal end of the light-receiving optical fiber 19 includes a ferrule 51 that covers a proximal end of the light-receiving optical fiber 19 and a flange 52 that fixes the ferrule 51 by allowing it to pass through a hole. Furthermore, the light-receiving connector receptacle 20*b* includes an optical fiber 53, a ferrule 54 that covers the optical fiber 53, a flange 55 that fixes a proximal end side of the ferrule 54 by allowing it to pass through a hole, and a cylindrical body 56 that holds a proximal end portion through which the ferrule 51 is inserted in an attached position.

Note that a proximal end face of the light-receiving optical fiber 19 becomes an emission end face that emits the received light, a lens (not shown) is provided on the proximal end face, a distal end face of the optical fiber 53 opposite to the proximal end face becomes an incident end face on which the received light is incident and a lens (not shown) is also provided on the distal end face.

Light incident on the distal end face of the optical fiber 53 is emitted to the photodetection section 21 from the emission end face of the proximal end. The body 3 is provided with an image processing section 60 that detects the light emitted from the proximal end of the optical fiber 53 and generates an image signal. The image processing section 60 is constructed of the photodetection section 21, and an amplifier 63*a* to a light-adjusting circuit 68 which will be described later.

A first dichroic mirror 61*a* and a second dichroic mirror 61*b* are disposed along an optical axis of the emission end face of the optical fiber 53. The first dichroic mirror 61*a* has a characteristic of selectively reflecting, for example, light of a red wavelength band and selectively transmitting light other than the light of the red wavelength band. On the other hand, the second dichroic mirror 61*b* has a characteristic of selectively reflecting, for example, light of a green wavelength band and selectively transmitting light other than the light of the green wavelength band.

The light of the red wavelength band reflected by the first dichroic mirror 61*a* is received by a photodetector 62*a* made up of a photodiode or the like and a photoelectrically converted red (R) electric signal is outputted to the amplifier 63*a*. The light of the green wavelength band reflected by the second dichroic mirror 61*b* is received by a photodetector 62*b* made up of a photodiode or the like and a photoelectrically converted green (G) electric signal is outputted to an amplifier 63*b*.

The light of the blue wavelength band that passes through the second dichroic mirror 61*b* is received by a photodetector 62*c* made up of a photodiode or the like and a photoelectrically converted blue (B) electric signal is outputted to an amplifier 63*c*. Thus, the photodetectors 62*a*, 62*b* and 62*c* generate R, G and B color signals and the generated R, G and B color signals are amplified by the amplifiers 63*a*, 63*b* and 63*c* respectively and then converted to digital color signals by A/D converters 64*a*, 64*b* and 64*c*.

Gains of the amplifiers 63*a*, 63*b* and 63*c* can be variably set from an input section 50 made up of a keyboard or the like via the control circuit 51. For example, it is possible to achieve a good color balance condition by inputting commands from a keyboard or the like (that makes up the input section 50) to set the values of the gains of the amplifiers 63*a*, 63*b* and 63*c* so as to illuminate a white object which serves as a reference so that an image formed by received reflected light of the white reference object appears white. In this case, when the white object is illuminated in advance, the amount of light is adjusted so that a light amount ratio among red, green and blue illuminating light beams as illuminating light beams of a plurality of wavelength bands emitted from the distal end face of the illumination optical fiber 10 becomes a predetermined ratio of amount of light (see FIG. 5B).

The digital R, G and B color signals generated by the A/D converters 64*a*, 64*b* and 64*c* are inputted to an auto gain control circuit (abbreviated as "AGC circuit") 65, and when the amplitude of the input signal is small, the AGC circuit 65 performs auto gain control in accordance with the amplitude of the input signal and outputs R, G and B color signals having predetermined amplitude. Note that the AGC circuit 65 performs (AGC) control on the R, G and B color signals with a common gain.

The R, G and B color signals outputted from the AGC circuit 65 are inputted to a pixel array processing circuit 66.

As described above, since an optical spot emitted from the distal end face of the illumination optical fiber 10 to scan the subject 5 side via the illumination lens 13 is scanned along a spiral-shaped track, the R, G and B color signals which are reflected light beams of the optical spot and received by the light-receiving optical fiber 19, photoelectrically converted by the photodetection section 21 and inputted to the pixel array processing circuit 66 become signals in a pixel array corresponding to the spiral-shaped track. For this reason, the pixel array processing circuit 66 performs pixel array processing as processing of converting the signals in a pixel array corresponding to the spiral-shaped track to image signals in a standard pixel array compatible with a raster scan scheme (which is used for a standard display apparatus).

The image signal in the standard pixel array compatible with the raster scan scheme generated by the pixel array processing circuit 66 (hereinafter simply referred to as "image signal") is passed through a correction circuit 67 that performs contour emphasis, gamma correction or the like and then outputted to the color monitor 4. The color monitor 4 displays an image corresponding to the inputted image signal on its display screen as a scanning type endoscope image.

The pixel array processing circuit 66 generates, for example, a luminance signal Y from the R, G and B color signals that form the image signal (according to Y=0.3R+0.59G+0.11B). The pixel array processing circuit 66 further includes a brightness calculation circuit 66a that calculates an average value Yav of the luminance signal Y over a period of several frames and uses this average value Yav as brightness or a brightness signal to be calculated (detected) as brightness B of the image displayed on the color monitor 4.

The brightness calculation circuit 66a outputs the generated brightness signal to a light-adjusting circuit 68. The light-adjusting circuit 68 includes a target brightness setting circuit 68a that sets target brightness which can set user-desired target brightness T of an image, for example.

The target brightness setting circuit 68a has a function as a target value setting section that sets an amount of illuminating light emitted from the distal end face of the illumination optical fiber 10 to a target amount of illuminating light. Note that a target value setting circuit having a function as a target value setting section may also be provided outside the target brightness setting circuit 68a.

The light-adjusting circuit 68 calculates a difference value between the target brightness T of the image and the brightness B of the image calculated (detected) by the brightness calculation circuit 65a, outputs a difference value signal for setting the difference value to 0 as a light adjustment signal to the laser drive circuit 25, the distance adjusting circuit 39 and the AGC circuit 65 and controls operations thereof. The target brightness T of the image becomes a target value with respect to the average value Yav, and since this target value is made up of brightness of red (R), green (G) and blue (B) image components, the amounts of light of red (R), green (G) and blue (B) are changed while keeping a predetermined ratio of amount of light of red (R), green (G) and blue (B) set at the time of white balance, and the amount of light is adjusted to the amount of light of the target brightness T of the image (see FIG. 5C).

Note that instead of the light-adjusting circuit 68 directly outputting a light adjustment signal to the laser drive circuit 25, the distance adjusting circuit 39 and the AGC circuit 65 and controlling operations thereof, the light-adjusting circuit 68 may output a light adjustment signal to the control circuit 51 and the control circuit 51 may have a function as a control section that controls operations of the laser drive circuit 25, the distance adjusting circuit 39 and the AGC circuit 65.

According to the present embodiment, for example, when a white object which serves as a reference is illuminated, to allow illuminating light beams of a plurality of wavelength bands emitted from the distal end face of the illumination optical fiber 10 to be respectively emitted with target values under a condition that satisfies a predetermined ratio of amount of light, the light-adjusting circuit 68 has a function as a control section that variably controls the value of the gap G which is a distance between the first lens 34 and the second lens 42 so that, for example, the amount of red light as the light of a first wavelength band and the amount of green or blue light as the light of a second wavelength band have a predetermined ratio of amount of light, such that the red light has a predetermined amount of light. In the present embodiment, the light beams of the three wavelength bands are variably controlled so that the illuminating light beams of the three wavelength bands emitted from the distal end face of the illumination optical fiber 10 can be respectively emitted with a target value under a condition that satisfies the predetermined ratio of amount of light.

Furthermore, in the present embodiment, as described above, the scanner 14 two-dimensionally vibrates the distal end of a single-mode fiber of the illumination optical fiber 10 that forms an optical transmission section, two-dimensionally scans illuminating light made up of light beams of three wavelength bands including the light of the first wavelength band and the light of the second wavelength band radiated onto the subject 5, receives the reflected light of the illuminating light radiated onto the subject 5 using the light-receiving optical fiber 19, the image processing section 60 generates an image signal of the subject 5 corresponding to the two-dimensional scanning from the electric signals photoelectrically converted by the photodetectors 62a, 62b and 62c, the brightness calculation circuit 66a provided in the image processing section 60 calculates brightness of the image from the image signal, further the control circuit 51 or the light-adjusting circuit 68 making up a control section performs control to adjust the gap G and adjust the amount of light emitted by the laser diodes 24a, 24b and 24c so that the brightness of the image matches the target brightness while maintaining a state in which the light amount ratio of three wavelength bands including the light of the first wavelength band and the light of the second wavelength band emitted from the distal end (face) of the illumination optical fiber 10 satisfies a predetermined ratio of amount of light.

The endoscope system 1 in such a configuration includes the insertion portion 6 that is inserted into the interior of the subject 5, the illumination optical fiber 10 that forms an optical transmission section that is provided in the insertion portion 6, transmits illuminating light incident on a proximal end to a distal end and emits the illuminating light from the distal end to thereby illuminate the interior of the subject 5, the light source section 22 configured to generate the light of the first wavelength band and the light of the second wavelength band which is different from the light of the first wavelength band as the illuminating light for illuminating the interior of the subject 5, the first lens 34 that forms a first lens section which receives, as incident light, the light of the first wavelength band and the light of the second wavelength band generated by the light source section 22 and emits the light with characteristics of spatially different spatial intensity distributions in accordance with the wavelength (beam waist size, beam waist position or the like), the second lens 42 that forms a second lens section which is provided opposite to the first lens section, receives, as incident light, at least part of the light emitted from the first lens section and causes the incident light to enter the proximal end of the optical transmission section, the distance adjusting circuit 39 that forms a distance adjusting section which adjusts the distance between the first lens section and the second lens section, and the light-adjusting circuit 68 or the control circuit 51 that forms a control section which controls the distance between the first lens section and the second lens section so that the amount of the light of the first wavelength band and the amount of the light of the second wavelength band emitted from the distal end of the optical transmission section have a predetermined ratio of amount of light and so that at least light of one wavelength band has a predetermined amount of light (by the distance adjusting section adjusting the distance between the first lens section and the second lens section based on the LUT 48a or 52a that forms a table storage section which stores a table showing a relationship between connection efficiency which is a ratio of the amount of light emitted from the distal end of the optical transmission section to the amount of light emitted from the first lens section regarding the light of the first wavelength band and the light of the second wavelength band, and the distance between the first lens section and the second lens section). Note that the configuration of the endoscope system 1 may be a basic configuration without the portion enclosed by parentheses.

Next, operation of the present embodiment will be described with reference to FIG. 5A. The scanning type endoscope 2 shown in FIG. 1 is connected to the body 3 and a power switch, which is not shown, of the body 3 is turned ON to bring the system into an operating state. When the connector 7 of the scanning type endoscope 2 is connected to the connector receptacle 8 of the body 3, the illuminating light connector 11 and the illuminating light connector receptacle 12 are connected together as shown in FIG. 2B (connection efficiency E becomes 1).

As shown in first step S1, the scanner 14 two-dimensionally vibrates (scans) the distal end of the illumination optical fiber 10 for a white object which serves as a reference, for example. The laser drive circuit 25 drives the laser diodes 24a, 24b and 24c to emit light intermittently. The light beams generated in the laser diodes 24a, 24b and 24c are transmitted to the illumination optical fiber 10, forming an optical spot on the object along a spiral-shaped scanning track from the distal end of the illumination optical fiber 10.

As shown in next step S2, the image processing section 60 of the body 3 generates an image signal. The reflected light of the optical spot radiated onto the object is received by the light-receiving optical fiber 19 and converted to an electric signal via the photodetection section 21 in the body 3.

Furthermore, the pixel array processing circuit 66 that makes up the image processing section 60 generates an image signal. The image signal is outputted to the color monitor 4 via the correction circuit 67. As shown in step S3, the color monitor 4 displays the image as an endoscope image.

In next step S4, the light-adjusting circuit 68 adjusts the amount of illuminating light when performing white balance. The adjustment of the amount of light is followed by white balance. The insertion portion 6 is inserted into the interior of the subject 5.

As shown in next step S5, the brightness calculation circuit 66a calculates brightness of the image, sends the brightness to the light-adjusting circuit 68 and the light-adjusting circuit 68 generates a light adjustment signal so that the calculated brightness of the image becomes target brightness and performs light adjustment.

Figure 5A:
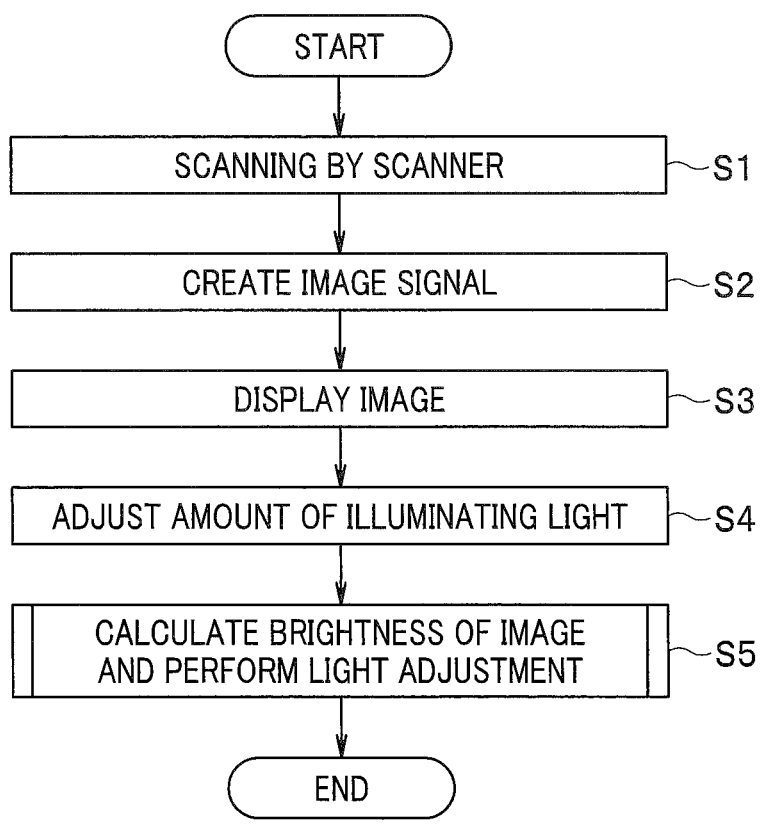
FIG. 5A is a flowchart illustrating entire processing of the first embodiment.
Figure 5B:
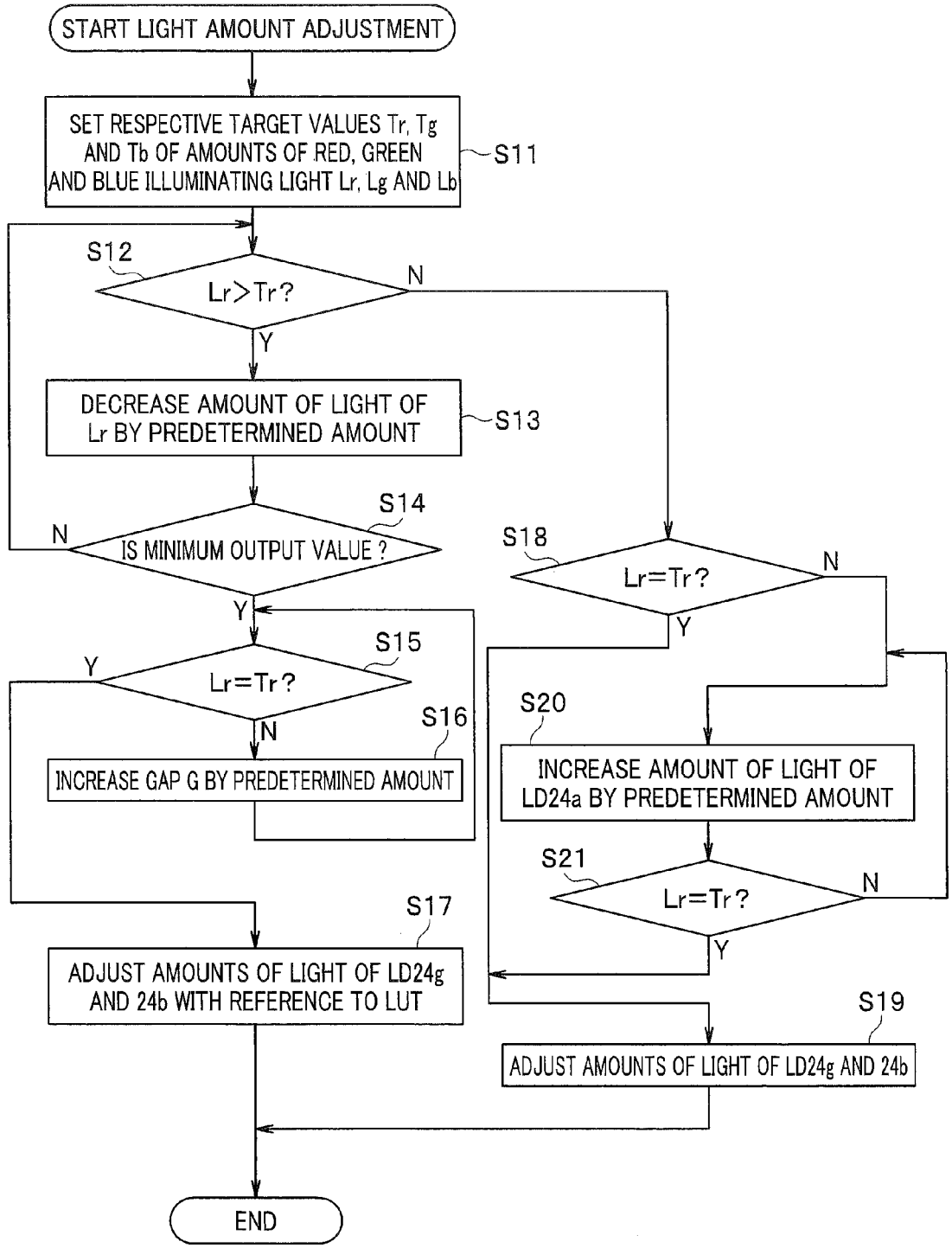
FIG. 5B is a flowchart illustrating detailed contents of light adjustment processing in FIG. 5A.

FIG. 5B illustrates details of the adjustment of the amount of light in step S4.

In first step S11, (the target value setting circuit in) the light-adjusting circuit 68 sets target values Tr, Tg and Tb corresponding respectively to the amounts of red, green and blue illuminating light beams Lr, Lg and Lb as light beams of a plurality of wavelength bands emitted from the distal end face of the illumination optical fiber 10. Note that the ratio among the target values Tr, Tg and Tb of red, green and blue light beams may be set to an equal ratio such as 1:1:1.

In next step S12, the light-adjusting circuit 68 determines, based on the amount of light with which the light amount adjusting circuit 25a of the laser drive circuit 25 causes the laser diode 24a to emit light, whether or not the amount of red illuminating light Lr emitted from the distal end face of the illumination optical fiber 10 is greater than the target value Tr, that is, whether Lr>Tr. Note that the light amount adjusting circuit 25a may send information on the amount of light with which the laser diode 24a is caused to emit light to the light-adjusting circuit 68, and the light-adjusting circuit 68 may determine whether Lr>Tr with reference to the information.

When the determination result shows that the condition of Lr>Tr is satisfied, in next step S13, the light-adjusting circuit 68 controls operation of the light amount adjusting circuit 25a of the laser drive circuit 25 so as to decrease the amount of light emitted by the laser diode 24a by a predetermined amount.

In next step S14, the light-adjusting circuit 68 or the laser drive circuit 25 determines whether or not the amount of light emitted from the laser diode 24a is a minimum output value. When the determination result shows that the amount of light is not a minimum output value, the flow returns to the process in step S12 and repeats the same process. When the minimum output value is reached, the light-adjusting circuit 68 determines whether or not the condition Lr=Tr is satisfied as shown in step S15.

When the determination result shows that the condition Lr=Tr is not satisfied (that is, the determination result Lr>Tr remains unchanged), in next step S16, the light-adjusting circuit 68 increases the gap G by a predetermined amount (slightly decreases the connection efficiency E) via the distance adjusting circuit 39. The flow then returns to the process in step S15.

In a condition with such a small amount of light, since the amount of red illuminating light emitted from the distal end face of the illumination optical fiber 10 sequentially decreases by gradually increasing the gap G, it is possible to make a setting so as to satisfy the condition of Lr=Tr.

When the condition of Lr=Tr is satisfied, the light-adjusting circuit 68 refers to, for example, the information of the LUT 52a in step S17, controls the operation of the light amount adjusting circuit 25a of the laser drive circuit 25 so as to adjust the amount of light (laser output value) emitted by the remained laser diodes 24b and 24c, and the light amount adjusting circuit 25a adjusts the amounts of light emitted by the respective laser diodes 24b and 24c to amounts of light that match the target values Tg and Tb respectively. Thus, according to the present embodiment, the connection efficiency E can be decreased from 1 down to a sufficiently small value (0.1 or less) by increasing the gap G even when the laser diode 24a is set to a minimum output value and when the amount of illuminating light is excessively larger than the target value Tr, and therefore the amount of illuminating light can be adjusted to a target value. Furthermore, the amounts of light of the other laser diodes 24b and 24c can be adjusted to amounts of light that match the target values Tg and Tb respectively by adjusting the amount of light emitted (laser output value) with reference to the information of the LUT 52a.

Furthermore, when the determination result in step S12 shows that Lr>Tr is not true, the light-adjusting circuit 68 determines, in step S18, whether or not Lr=Tr. When the determination result shows that Lr=Tr, the light-adjusting circuit 68 controls the operation of the light amount adjusting circuit 25a of the laser drive circuit 25 in step S19, and the light amount adjusting circuit 25a adjusts the amounts of light respectively emitted by the laser diodes 24b and 24c as the laser diodes other than the laser diode 24a so as to match the respective target values Tg and Tb. By this means, the amounts of light can be set to target amounts of illuminating light.

When the determination result in step S18 shows that Lr=Tr is not true (that is, Lr<Tr), the light-adjusting circuit 68 controls the operation of the light amount adjusting circuit 25a in step S20 so as to increase the amount of light of the laser diode 24a by a predetermined amount.

In next step S21, the light-adjusting circuit 68 determines whether or not Lr=Tr. When the determination result shows that Lr=Tr is not true, the flow returns to the process in step S40 and repeats the same process.

When the determination result shows that Lr=Tr, the flow returns to the process in step S19 and the laser diodes 24b and 24c adjust the amounts of light emitted respectively so that the amounts of illuminating light beams Lg and Lb respectively emitted from the distal end face of the illumination optical fiber match the target values Tg and Tb respectively. The information set by the adjustment of the amounts of light in FIG. 5B is stored in the memory 52, for example. The information is referenced in the process in FIG. 5C. Note that FIG. 5B shows that the system can cover a wide range from a case where large target values Tr, Tg and Tb are set to a case where small target values Tr, Tg and Tb are set.

By this means, the light adjustment processing in FIG. 5B ends. By inputting a command for adjusting white balance from the input section 50 under the illuminating light set in this way, the control circuit 51 adjusts the gains of the three amplifiers 63a, 63b and 63c so that the R, G and B color signals outputted from the pixel array processing circuit 66 have equal signal levels to set a white balance state.

Figure 5C:
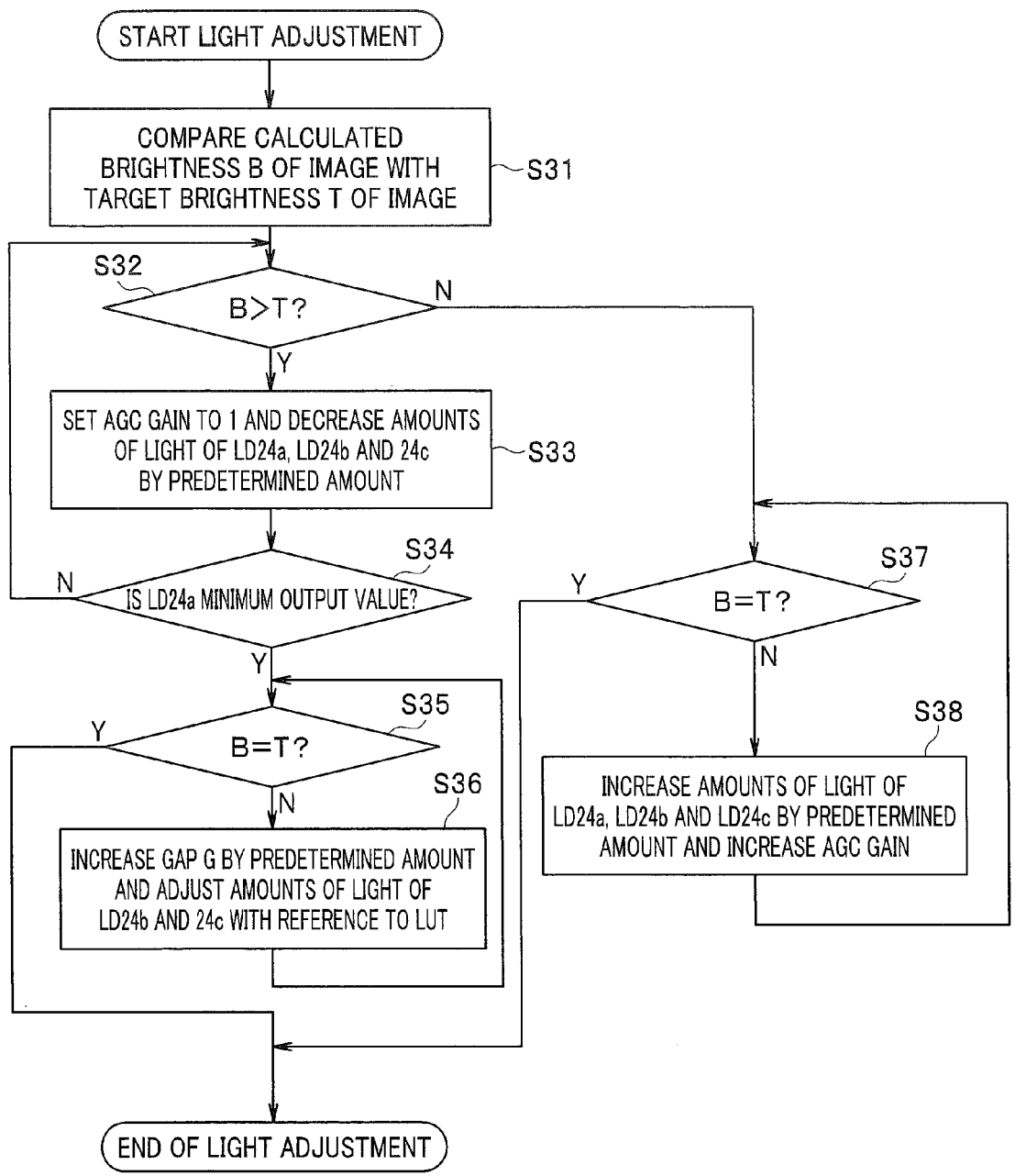
FIG. 5C is a flowchart illustrating processing of adjusting an amount of illuminating light.

After that, the insertion portion 6 is inserted into the interior of the subject 5 and the process in step S5 in FIG. 5A is executed. FIG. 5C illustrates details of the light adjustment process in this step S5.

When acquiring an endoscope image, the amount of illuminating light is generally increased to increase an SN ratio of an image signal detected. For this reason, a case will be described hereinafter as an example where the amounts of illuminating light set in FIG. 5B are set to the target values Tr, Tg and Tb by adjusting the amounts of light emitted from the three laser diodes 24a, 24b and 24c. Although the target values Tr, Tg and Tb may also be set to different values respectively, a case is mainly assumed and described where the respective targets values are equal, that is, a case where the amounts of illuminating light are set to the target values Tr=Tg=Tb, for clarity of description.

When the light adjustment process starts, the light-adjusting circuit 68 compares the calculated (detected) brightness B of the image with the target brightness T of the image as shown in step S31. In next step S32, the light-adjusting circuit 68 determines, from the comparison result, whether or not B>T. That is, the light-adjusting circuit 68 determines whether or not the calculated brightness B of the image is greater than the target brightness T of the image.

When the determination result shows B>T, in next step S33, the light-adjusting circuit 68 controls the AGC circuit 65 so as to decrease the gain to 1 and also controls (the light amount adjusting circuit 25a of) the laser drive circuit 25 so as to decrease the amounts of light emitted by the laser diodes 24a, 24b and 24c by a predetermined amount as small amounts of light.

In next step S34, the light-adjusting circuit 68 determines whether or not the amount of light emitted by the laser diode 24a is a minimum output value. When the amount of light is not a minimum output value, the flow returns to the process in step S32. By this means, light adjustment is performed by gradually decreasing the amounts of light emitted by the laser diodes 24a, 24b and 24c so that the calculated brightness B of the image is brought closer to the target brightness T of the image.

When the amount of light emitted by the laser diode 24a is a minimum output value, the light-adjusting circuit 68 determines, in next step S35, whether or not the condition of B=T is satisfied. When the determination result shows that the condition of B=T is not satisfied (that is, when B>T), the light-adjusting circuit 68 controls, in step S36, the operation of the distance adjusting circuit 39 and the distance adjusting circuit 39 increases the gap G by, for example, a predetermined amount (on the order of 10 μm to 20 μm) (in other words, slightly decreases the connection efficiency E).

Furthermore, the light-adjusting circuit 68 controls the operation of the light amount adjusting circuit 25a of the laser drive circuit 25 with reference to, for example, the information of the LUT 52a and the light amount adjusting circuit 25a adjusts the amounts of green and blue light beams so that the decrements in the amounts of light emitted by the remaining laser diodes 24b and 24c (laser output values) become equal to the decrement in the amount of the red light beam.

By this means, the amounts of red, green and blue illuminating light beams emitted from the distal end face of the illumination optical fiber 10 gradually decrease while maintaining the light amount ratio when white balance is performed (e.g., ratio of amounts of red, green and blue light beams is 1:1:1). Note that when the ratio of amounts of red, green and blue light beams is not equal, the light-adjusting circuit 68 performs control so that the respective amounts of light decrease at the same rate as the light amount ratio.

As described above, with the amount of light emitted by the laser diode 24a set to a minimum output value, the distance adjusting circuit 39 increases the gap G by a predetermined amount, decreases the amounts of red, green and blue light beams, and in that case, the light amount adjusting circuit 25a adjusts the amount of light emitted by the laser diodes 24b and 24c so as to correct a change of the decrement in the amount of light caused by the difference in the connection efficiency E in red, green and blue light beams (that is, equalizes the decrements in the amounts of red, green, blue light beams).

Thus, while gradually increasing the gap G when the amount of light is small (minimum output value), the amounts of red, green and blue illuminating light beams emitted from the distal end face of the illumination optical fiber 10 sequentially decrease, and it is thereby possible to set the amounts of red, green and blue illuminating light beams so as to satisfy the condition of B=T.

In other words, in the present embodiment, even when the laser diode 24a is set to a minimum output value, if the amount of illuminating light is excessively larger than the target brightness T of the image, the gap G is increased and the connection efficiency E is allowed to be decreased from 1 to a sufficiently small value (0.1 or less), and it is thereby possible to adjust the brightness to the target brightness T of the image.

Furthermore, when the determination result in step S32 shows that B>T is not true, the light-adjusting circuit 68 determines whether or not B=T in step S37. When the determination result shows that B=T, the process in FIG. 5C ends.

On the other hand, when the determination result shows that B=T is not true, in step S38, the light-adjusting circuit 68 controls the operation of the light amount adjusting circuit 25a of the laser drive circuit 25 and the light amount adjusting circuit 25a increases the amounts of light emitted by the laser diodes 24a, 24b and 24c by a predetermined amount respectively. The AGC gain is also incremented by a predetermined amount. After the process in step S38, the flow returns to the process in step S37. By this means, it is possible to set a state in which the target brightness is achieved. Note that in step S35 or S37, after the determination result of B=T is obtained, it may be detected whether or not there is any halation pixel region in the image and if there is a halation pixel region, the target brightness may be decreased so as to prevent any halation pixel region from being detected.

According to the present embodiment operating in this way, even when light beams of a plurality of different wavelength bands are used, it is possible to adjust the respective amounts of light to a predetermined ratio of amount of light. Furthermore, when the brightness of the image displayed on the color monitor 4 as the display apparatus changes, it is possible to automatically adjust the brightness of the image to the target brightness of the image which is suitable for a diagnosis or observation while maintaining (a predetermined ratio of amount of light as) the ratio of amounts of light of a plurality of wavelength bands emitted from the distal end face of the illumination optical fiber 10.

FIG. 4 illustrates a case where a maximum output value and a minimum output value of the three laser diodes 24a, 24b and 24c are 10 mW and 1 mW respectively, and the respective laser light sources have the same maximum output value and the same minimum output value. The present embodiment is also applicable to a case where the respective laser light sources have different maximum output values and different minimum output values. FIG. 6 illustrates examples of cases where the amount of illuminating light is set to, for example, 0.4 mW and 0.2 mW. Note that "c" in FIG. 6 indicates the value of the gap G at which the connection efficiency E is 0.4 in the case of red laser light as shown in FIG. 3.

Furthermore, the present embodiment can also adjust the amounts of illuminating light emitted from the distal end face of the illumination optical fiber 10 so that the amounts of illuminating light have values that differ among red, green and blue wavelength bands. FIG. 7 illustrates specific examples of cases where the amounts of illuminating light are adjusted (set) to values that differ among red, green and blue wavelength bands.

Note that an embodiment configured by omitting part of the aforementioned embodiment also belongs to the present invention.

What is claimed is:

1. An endoscope system comprising:
an optical transmission section that is provided in an endoscope inserted into an interior of a subject, transmits illuminating light incident on a proximal end to a distal end and emits the illuminating light from the distal end to illuminate the interior of the subject;
a light source section that generates light of a first wavelength band and light of a second wavelength band which is different from the light of the first wavelength band as the illuminating light for illuminating the interior of the subject;
a first lens section that receives, as incident light, the light of the first wavelength band and the light of the second wavelength band generated by the light source section and emits the light with characteristics of different spatial intensity distributions in accordance with wavelengths;
a second lens section that is provided opposite to the first lens section, receives, as incident light, at least part of the light emitted from the first lens section and causes the received light to enter the proximal end of the optical transmission section;
a distance adjusting section that can adjust a distance between the first lens section and the second lens section; and
a controller configured to control the distance adjusting section that adjusts the distance between the first lens section and the second lens section so that an amount of the light of the first wavelength band and an amount of the light of the second wavelength band emitted into the interior of the subject have a predetermined ratio of amount of light.

2. The endoscope system according to claim 1, further comprising a table storage section configured to store a table showing a relationship between connection efficiency which is a ratio of an amount of light emitted from the distal end of the optical transmission section to an amount of light emitted from the first lens section regarding the light of the first wavelength band and the light of the second wavelength band, and the distance between the first lens section and the second lens section,
wherein the controller adjusts the distance between the first lens section and the second lens section via the distance adjusting section based on the table stored in the table storage section.

3. The endoscope system according to claim 1, wherein the controller adjusts the distance between the first lens section and the second lens section via the distance adjusting section so that one of the light of the first wavelength band and the light of the second wavelength band has a predetermined value of amount of light and further controls an amount of light emitted by the light source that generates the other of the light of the first wavelength band and the light of the second wavelength band so that the other of the light of the first wavelength band and the light of the second wavelength band satisfies the predetermined ratio of amount of light.

4. The endoscope system according to claim 1,
wherein the light source section generates light with a connection efficiency higher than that of the light of the second wavelength band as the light of the first wavelength band, the connection efficiency being a ratio of an amount of light emitted from the distal end of the optical transmission section to an amount of light emitted from the first lens section, and the controller adjusts the distance between the first lens section and the second lens section via the distance adjusting section so that the light of the first wavelength band emitted from the distal end of the optical transmission section becomes a predetermined value of amount of light, and controls the amount of the light emitted by the light source that generates the light of the second wavelength band so that the light of the second wavelength band satisfies the predetermined ratio of amount of light.

5. The endoscope system according to claim 4, wherein the controller is further configured to:
   adjust amounts of light emitted of the light of the first wavelength band and the light of the second wavelength band; and
   make a setting so as to emit the light of the first wavelength band and the light of the second wavelength band from the distal end of the optical transmission section with a target value under a condition that satisfies the predetermined ratio of amount of light,
   wherein when the predetermined ratio of amount of the light of the first wavelength band and the light of the second wavelength band emitted from the distal end of the optical transmission section is set to 1:1 and the target value corresponding to the predetermined value of amount of light emitted from the distal end of the optical transmission section with respect to the light of the first wavelength band is set to be less than the minimum output value of the amount of the light emitted of the first wavelength band,
   the controller:
      sets the amount of the light emitted of the first wavelength band to a minimum output value,
      adjusts the distance between the first lens section and the second lens section via the distance adjusting section so that the light of the first wavelength band set to the minimum output value by the light amount adjusting section becomes the predetermined value of amount of light, and
      adjusts the amount of the light emitted of the second wavelength band so as to keep a state in which the light of the second wavelength band emitted from the optical transmission section satisfies the predetermined ratio of amount of light.

6. The endoscope system according to claim 4, further comprising:
   a scanner that two-dimensionally vibrates the distal end of the optical transmission section to two-dimensionally scan the illuminating light including the light of the first wavelength band and the light of the second wavelength band radiated onto the subject;
   an image processing section configured to receive the illuminating light reflected by the subject and generate an image signal of the subject from a photoelectrically converted electric signal; and
   a brightness calculation section provided in the image processing section and configured to calculate brightness of an image from the image signal of the subject,
   wherein while controlling an amount of light emitted from a first light source that generates the light of the first wavelength band and an amount of light emitted from a second light source that generates the light of the second wavelength band in the light source section so that the amount of the light of the first wavelength band and the amount of the light of the second wavelength band emitted from the distal end of the optical transmission section have a predetermined ratio of amount of light, the controller controls light adjustment including adjustment of the distance between the first lens section and the second lens section via the distance adjusting section and adjustment of the amount of light emitted of the second light source so that the brightness of the image matches the target brightness while maintaining the predetermined ratio of amount of light.

7. The endoscope system according to claim 6, further comprising a table storage section configured to store a table showing a relationship between the connection efficiency and the distance between the first lens section and the second lens section,
   wherein in a case where the controller controls the light adjustment, even in a state in which the amount of the light emitted of the first wavelength band generated by the first light source is set to a minimum output value which is a minimum amount of light emitted, if the brightness of the image calculated by the brightness calculation section is greater than the target brightness, the controller repeatedly performs control by increasing the distance between the first lens section and the second lens section by a predetermined amount via the distance adjusting section with the amount of the light emitted of the first wavelength band being set to the minimum output value, decreasing the amount of the light of the first wavelength band emitted from the distal end of the optical transmission section, and further adjusting the amount of the light emitted of the second wavelength band from the second light source so as to satisfy the predetermined ratio of amount of light before decreasing the amount of the light of the first wavelength band based on information of the table.

8. The endoscope system according to claim 1,
   wherein the optical transmission section is made of a single-mode fiber, and
   the light source section generates laser light as the light of the first wavelength band and the light of the second wavelength band.

9. The endoscope system according to claim 1,
   wherein the light source section comprises:
   a red color laser diode that generates red color laser light belonging to a red wavelength band as a first light source that generates the light of the first wavelength band; and
   a green color laser diode that generates green color laser light belonging to a green wavelength band as a second light source that generates the light of the second wavelength band and a blue color laser diode that generates blue color laser light belonging to a blue wavelength band, and
   the controller adjusts the distance between the first lens section and the second lens section via the distance adjusting section so that the amount of the red color laser light, the amount of the green color laser light and the amount of the blue color laser light emitted from the distal end of the optical transmission section have the predetermined ratio of amount of light, and so that the amount of the red color laser light becomes a predetermined value of amount of light.

10. The endoscope system according to claim 9, further comprising:
    a table storage section configured to store a table showing a relationship between connection efficiency which is a ratio of an amount of light emitted from the distal end of the optical transmission section to an amount of light emitted from the first lens section regarding the red color laser light, the green color laser light and the blue color laser light, and the distance between the first lens section and the second lens section;

the controller being configured to:

adjust amounts of light emitted of red color laser light generated by the red color laser diode, green color laser light generated by the green color laser diode and blue color laser light generated by the blue color laser diode; and make a setting so that the red color laser light, the green color laser light and the blue color laser light are respectively emitted from the distal end of the optical transmission section with target values under a condition that satisfies the predetermined ratio of amount of light, wherein when the target value of the red color laser light emitted from the distal end of the optical transmission section set by the target value setting section is set to be less than a minimum output value of the red color laser light that can be generated by the red color laser diode, the controller:

sets the amount of light emitted of the red color laser light by the red color laser diode to the minimum output value, adjusts the distance between the first lens section and the second lens section via the distance adjusting section with reference to the information of the table so that the red color laser light set to the minimum output value by the light amount adjusting section has the predetermined value of amount of light, and adjusts the amount of light emitted of the green color laser light by the green color laser diode and the amount of light emitted of the blue color laser light by the blue color laser diode so as to keep, with reference to the information of the table, a state in which the amount of the green color laser light and the amount of the blue color laser light emitted from the optical transmission section satisfy the predetermined ratio of amount of light.

11. The endoscope system according to claim 10, further comprising:

a scanner that two-dimensionally vibrates the distal end of the optical transmission section to two-dimensionally scan the illuminating light including the light of the first wavelength band and the light of the second wavelength band radiated onto the subject;

an image processing section configured to receive the illuminating light reflected by the subject and generate an image signal of the subject from a photoelectrically converted electric signal; and a brightness calculation section provided in the image processing section and configured to calculate brightness of an image from the image signal of the subject, wherein while controlling the amount of light emitted from the red color laser light, the amount of the green color laser light and the amount of the blue color laser light emitted from the distal end of the optical transmission section to a predetermined ratio of amount of light, the controller controls light adjustment including adjustment of the distance between the first lens section and the second lens section via the distance adjusting section so that the brightness of the image matches the target brightness while maintaining the predetermined ratio of amount of light; and adjustment of respective amounts of light emitted of the red color laser diode, the green color laser diode and the blue color laser diode.

* * * * *